United States Patent [19]

Jindra et al.

[11] 4,001,454
[45] Jan. 4, 1977

[54] FLAVORING FOODS WITH 8-METHYL-NON-2YNOL AND ITS DERIVATIVES

[75] Inventors: Henri Jindra, Geneva, Switzerland; William Patrick Clinton, Monsey, N.Y.

[73] Assignee: General Foods Corporation, White Plains, N.Y.

[22] Filed: May 28, 1975

[21] Appl. No.: 581,451

[52] U.S. Cl. .......................... 426/534; 260/600 R; 260/615 A; 260/632 Y; 260/488 H
[51] Int. Cl.$^2$ ........................................ A23L 1/226
[58] Field of Search ................ 426/534; 260/632 Y

[56] References Cited

UNITED STATES PATENTS 3,655,397   4/1972   Parliment et al. .................. 426/534
3,754,936   8/1973   Epstein ............................. 426/534

OTHER PUBLICATIONS

Perfume and Flavor Chemicals, Aretander, 1969, Published by the Author, Montclair, N.J., Items Numbered 2107, 2113, 2114, 2116, 2381, 2448.

*Primary Examiner*—Joseph M. Golian
*Attorney, Agent, or Firm*—Daniel J. Donovan

[57] ABSTRACT

A new alcohol, 8-methyl-non-2ynol and its derivatives has been discovered having a woody taste and flavor, and useful for enhancement of foodstuffs. The enhancement is achieved by the addition of a small but effective amount of said compounds to the food.

13 Claims, No Drawings

FLAVORING FOODS WITH 8-METHYL-NON-2YNOL AND ITS DERIVATIVES

BACKGROUND OF THE INVENTION

The present invention relates to 8-methyl-non-2ynol the corresponding aldehyde, esters of organic acids and the alcohol in which the carbonyl is not conjugated with a double bond or aromatic ring and acetals of the aldehyde found useful in the area of flavor alteration whether by enhancement of flavor characteristics in a substance, modification of flavor or by complete or partial masking of flavor. Still more particularly, the invention relates to incorporation of woody flavor compounds selected from the group consisting of 8-methyl-non-2-ynol, esters of 8-methyl-non-2ynol and lower alkyl organic acids such as formic, acetic, etc. in which the carbonyl is not conjugated with a double bond or aromatic ring, 8-methyl-non-2ynal and its acetals and mixtures thereof in coffee to reduce the caramel, acid, and sour flavor of coffee; modify and improve the green, earthy, and buttery notes of coffee; and add a desirable woody, regular coffee flavor to the foodstuff. The compounds employed have particular application to soluble and regular coffee which may be deficient in a woody flavor.

DESCRIPTION OF THE PRIOR ART

In the field of flavor enhancement, it has been general practice to employ synthetic and naturally isolated compounds and compositions to enhance or mask the flavor of foodstuffs. Generally, isolation of single flavors does not allow one to predict equivalent flavors since compounds of greatly differing structure have been found to produce approximately the same flavor character while compounds of similar structure frequently differ appreciably in taste. Consequently, the identification of desirable flavor components requires synthesis and trial of individual candidates until compounds are identified which have desirable flavors.

For many years, coffee technologists have searched for flavor enhancing compounds which would produce the flavor note generally described by coffee experts as "woody." Recently, a number of woody flavored 2-nonenals and 2-nonenols have been identified in U.S. Pat. No. 3,655,397, to have this character. In the course of investigating those compounds and others, we have discovered the compounds employed in the composition and process of this invention.

SUMMARY OF THE INVENTION

The general purpose of this invention is to provide compounds and compositions containing compounds which will enhance coffee flavored foodstuffs by imparting to them a regular coffee flavor characterized by experts as woody.

The flavor enhancement is achieved by the addition of a small but effective amount of woody flavored compounds to the foodstuff to be flavored. The compounds, singly or mixtures, produce a coffee flavor when added in minute amount, generally in parts per billion, to water or foodstuffs.

It is an object of this invention to provide compounds for the flavor alteration of foodstuffs, particularly coffee deficient in woody flavor.

It is a further object of this invention to describe processes for employing woody compounds in concentrates useful for enhancing the flavor of foodstuffs, particularly coffee.

DESCRIPTION OF THE INVENTION

The compounds employed are characterized by the following formulas:

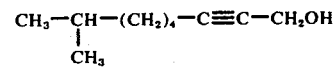

esters of organic acids and the preceding compound I;

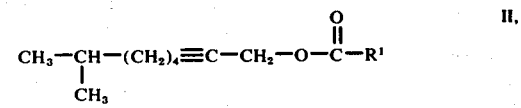

where R1, is hydrogen or lower alkyl or substitute lower alkyl, 8-methyl-non-2ynal;

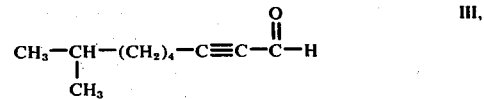

acetals of 8-methyl-non-2ynal;

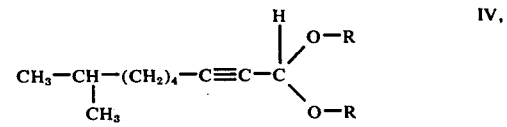

Where R is lower alkyl or substituted lower alkyl.

Prop-1-ynol was added to dihydropyran in the presence of hydrochloric acid to give prop-1-ynyltetrahydropyranyl ether. The ether was alkylated with 5-methylhexyl bromide. The resultant product was hydrolyzed with sulfuric acid to the desired alcohol, 8-methylnon-2yn-1-ol.

Oxidation of 8-methylnon-2yn-1-ol with manganese dioxide in refluxing ether gave 8-methylnon-2yn-1-al. The aldehyde was converted to acetals using appropriate acidic catalysts.

Representative of the woody compound of this invention are 8-methyl-non-2yn-1-ol, 8-methyl-non-2yn-1-al, 8-methyl-non-2yne dimethylacetal, 8-methyl-non-2yne diethyl acetal, 8-methyl-non-2ynyl acetate, 8-methyl-non-2ynyl isobutylate, 8-methyl-non-2ynyl phenylacetate and the like.

The compounds for Formulas I, II, III and IV are useful for enhancing the flavor of food. The compounds are particularly useful to enhance coffee flavored foodstuffs where a regular coffee flavor generally characterized by coffee experts as woody is desired but deficient—such as regular coffees like Robustas, decaffeinated coffee, soluble coffee; and coffee flavored foods such as icings, drinks, Postum brand beverage, desserts, candies, and the like.

The compounds of Formulas I–IV and mixtures thereof give coffee flavor when added to water or foodstuffs. In addition to imparting to coffee a regular, coffee-like flavor having a strong woody note, these compounds exert a balancing effect on other desirable coffee notes such as the green, earthy, and buttery flavors while masking the undesirable acid, sour, and caramel flavors. The compounds also exert a blending effect of the overall brew flavor of soluble coffee. The compounds of Formulas I–IV may be added to any coffee including soluble coffee, decaffeinated coffee either regular or soluble and regular roasted and ground coffee. The compounds of Formulas I to IV may also be incorporated with other coffee flavor fractions, both synthetic and those obtained from coffee, and with these flavors exert a balancing effect while strengthening the woody regular coffee flavor.

Depending on the flavor desired, the compounds of Formulas I to IV can be incorporated in the foodstuff either alone, combined with other flavor ingredients, or with carriers. In flavoring soluble coffee, the woody compounds may be either added to regular coffee prior to extraction, to coffee percolate prior to drying, or may be plated on or mixed with the dried coffee. Since only a minute amount of the flavor and aroma compounds are needed, it is preferred to incorporate them in an edible carrier or concentrate prior to addition to the coffee. The concentrate or carrier may be liquid, syrup, or solid, depending on its ultimate use. For example, the compounds of Formulas I to IV may be incorporated in ethanol, propylene glycol; oils such as cottonseed, coffee, peanut or the like; or other edible vehicles to form a concentrate for convenient shipping, storage, and addition to the foodstuff. For example, oil containing a compound of Formulas I to IV or mixtures thereof may be plated on soluble coffee to enhance its flavor or alternatively, an oil containing the flavor compound may be incorporated in extract and dried. Dry concentrates containing the compounds of Formulas I to IV or mixtures thereof may also be prepared by employing film-forming compositions such as gums—like gum arabic, pectins, alginates, and the like; starch breakdown products such as Capsul (National Starch), Morex 1918 (Corn Products), Maltrin 10 (Grain Processing), and the like; candy melt systems and other art-recognized stabilizing or diluent systems. In forming any concentrate, the proportions of the compounds of Formulas I to IV therein is not critical provided the level of flavoring is controlled to give an enhanced coffee flavor and an even distribution of the flavor concentrate throughout the foodstuff to be flavored.

Minute amounts of the compounds of Formulas I to IV are sufficient to produce an enhancement of coffee flavor in foodstuffs. For example, in regular or soluble coffee beverages, say from about 1 to 1.5% coffee solids, the compounds can be employed to produce a change in cup flavor and aroma but a change which cannot be described as a particular flavor. Alternatively, proportions sufficient to be recognized as woody may be employed. The threshold flavor level for the compounds of this invention is about 30ppm with a woody flavor evident at about 75ppm on a dry coffee solids basis.

The flavor impact of the compounds of Formulas I to IV and mixtures thereof is easily adjusted by varying the concentration of the flavoring compounds employed in the foodstuff. It is to be expected that adjustment will be necessary depending on the particular foodstuffs being flavored. Initial panel screening by those of ordinary skill in the art is used to determine the threshold and proper strength level for the particular foodstuff in which the flavor is employed.

The compounds of Formulas I to IV are particularly useful for balancing the natural flavor of spray dried and freeze-dried soluble coffee, decaffeinated coffee, both soluble and regular, and regular coffee of various blends or single varieties, particularly those having high Robusta content. The flavor compounds are particularly preferred for imparting a woody flavor to the preceding coffees deficient, partially or totally, in that flavor. However, even at levels below the woody threshold level, balancing of flavor is noted by expert tasters. The flavor compounds of Formulas I to IV are also particularly useful when combined with steam-generated natural coffee aromas or enhancers where there is produced a blending or smoothing of coffee aroma and flavor and a masking of the undesirable sourness and caramel characteristics often associated with coffee. Similar improvement is noted for mixtures of synthetic and natural coffee aromas and flavors. In addition to the application of the compounds of Formulas I and IV in foodstuffs, these flavoring agents may also be employed in edible substances such as pharmaceuticals, where a woody regular coffee note is desired.

The invention is now illustrated but not limited by the following examples:

EXAMPLE I

8-methylnon-2-yn-1-ol 168g. (3 mole) of prop-1-ynol were added with stirring to a mixture of 269g. (3.2 mole) of anhydrous dihydropyran and 0.5 ml of concentrate hydrochloric acid. The reaction is exothermic and the temperature is maintained at 60° C by external cooling when the addition is complete, the mixture is further maintained with stirring for 1 hour whereupon it is washed with dilute sodium carbonate. Distillation afforded 372g. (89%) of prop-1-ynltetrahydropyranyl ether, b.p. 65°–6° C/10mm.

70g. (0.5 mole) of prop-1-ynyltetrahydropyranyl ether in 200 ml of dimethyl sulfoxide were added with stirring to a solution of 11.5g. (0.5 mole) of lithium amide in 200 ml of dimethyl sulfoxide. Stirring was continued for 1 hour and 5-methylhexyl bromide 89g. (0.5 mole) were added over 45 min. External cooling was necessary to keep the temperature at 30° C. After 3 hours, the mixture was poured into 1 liter of ice-water. The mixture was extracted with petrol-ether, and the organic phase washed with 10% sulfuric acid, and then water. The solution was dryed over magnesium sulfate concentrated and distilled at 100°–103° C/0.01mm to give 82.6 (70%) of 8-methylnon-2-ynyl tetrahydropyranyl ether.

A mixture of 13g. (0.5 mole) of 8-methylnon-2-ynyl-tetrahydropyranyl ether and 250 ml of 10% sulfuric acid was heated at 90° C for ½ hour. Steam distillation gave 800 ml of distillate which, by extraction with petrol-ether, washing with water, drying over magnesium sulfate and concentrate gave on vacuum distillation 7.6g. (90%) of 8-methylnon-2-ynol, b.p. 67°–8° C/0.01mm.

NMR: 0.8 (3H,s), 0.92 (3H,s) 1.32 (7H,m), 2.16 (2h,m), 4.18 (2H,s) 4.33 (1H,s) δ ppm;

IR: 3320 and 2220 cm$^{-1}$;

MS: m/e : 43 (100), 41 (87.5), 55 (76), 67 (53.6), 93 (38), 121 (8.4), 123 (7.8), 111 (4.7).

EXAMPLE II

8-Methylnon-2-yn-1-al

Five gms. (0.033 mole) of 8-methylnon-2-yn-1-al was added to a vigorously stirred mixture of 50 gms. (0.57 mole) of manganese dioxide in 500 ml of ether (cooled in ice water). After 1 hour the ice bath was removed and the mixture stirred for 5 hours. The manganese dioxide was filtered and the ether distilled. The residue was purified by vacuum distillation to give 8-methyl-non-2-yn-1-al.

EXAMPLE III 1,1-dimethoxy-8-methylnon-2-yne

One gm. (0.007 mole) of 8-methylnon-2-yn-1-al, 10 gm. (0.1 mole) of trimethylorthoformate and 0.2 g of para-toluene-sulfuric acid were distilled. Methyl formate and methyl alcohol were collected. The solution was diluted with 15 ml of water and extracted with ether. The ether solution was washed with 5% sodium bicarbonate, and then water. The ether extract was dried over sodium sulfate, concentrate and distilled under vacuum to give 1,1-dimethoxy-8-methyl-non-2-yne.

EXAMPLE IV 2-(7-methyloct-2-yne) dioxolane 2 gm. (0.014 mole) of 8-methylnon-2-yn-1-al, 3 gm. (0.02 mole) triethylorthoformate, 2.5 gm. (0.04 mole) of ethylene glycol and 0.1 g of ammonium chloride were distilled. Ethyl formate and ethyl alcohol were collected. The solution was diluted with 20 ml. of water and extracted with ether. The ether extract was washed with 5% sodium bicarbonate and then water. The ether extract was dried over sodium sulfate contrate and distilled under vacuum to give 2-(7-methyloct-2-yne) dioxolane.

EXAMPLE V

Roasted coffee extract is prepared from roasted coffee by normal commercial techniques to obtain a percolate of 15–50% coffee soluble solids. Sufficient 8-methyl-non-2-ynol is added to give a woody, natural coffee flavor at 1.2% coffee solids in aqueous solution. The mixture is placed in cooled trays and frozen at a thickness of less than one-half inch. A frozen mixture of extract and aroma is then freeze dried in a commercial drying unit to produce a freeze-dried coffee having enhanced woody flavor.

Instead of freeze drying the enhanced percolate, it may be spray dried instead. If desired, a portion of the percolate may be employed to fix the flavor compound by any known drying procedure and then mixed with unenhanced dried soluble coffee.

EXAMPLE VI

To 8 ounces of boiling water is added 2.84g. Instant Maxwell House (IMH) brand soluble coffee to give a 1.2% solids solution. To this solution is added portions of a 1% by weight solution of 8-methyl-non-2ynol in ethanol until a threshold flavor level and flavor intensity is determined. Portions of 1, 5, 20, 25 and 30 microliters of the 1% solution are added to 8 oz. cups of IMH. The threshold flavor is evident to two expert tasters at 30ppm (10 microliters of 1% solution) with a woody flavor evident at 75ppm.

What is claimed is:

1. A process fpr enhancing the woody flavor of foodstuffs comprising adding thereto a compound selected from the formula:

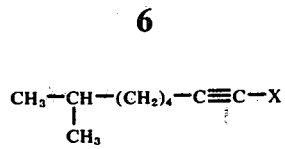

Where X is selected from the group consisting of $CH_2OH$,

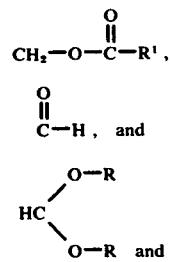

where R' is hydrogen, lower alkyl or substituted lower alkyl and R is alkyl or substituted lower alkyl in a small but effective amount to give a woody flavor.

2. The process of claim 1 in which the foodstuff is coffee.

3. The process of claim 2 in which the coffee is decaffeinated.

4. The process of claim 2 in which the coffee is roasted coffee.

5. The process of claim 2 in which the coffee is soluble coffee.

6. The process of claim 2 in which the compound is 8-methyl-non-2yn-1-ol.

7. The process of claim 6 in which the coffee is soluble coffee.

8. The process of claim 7 in which the soluble coffee is deficient in a woody flavor.

9. A foodstuff having as an active woody flavoring ingredient a compound selected from the formula:

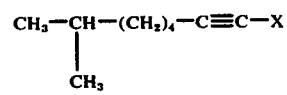

Where X is selected from the group consisting of $CH_2OH$,

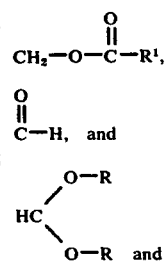

where R' is hydrogen, lower alkyl or substituted lower alkyl and R is alkyl or substituted lower alkyl in a small but effective amount to give a woody flavor.

10. The foodstuff of claim 9 wherein the foodstuff is coffee deficient in woody flavor.

11. A process for balancing the flabor of roasted coffee products by adding thereto a compound selected from the formula:

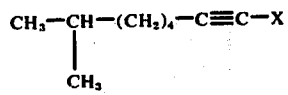

Where X is selected from the group consisting of CH$_2$OH,

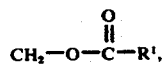

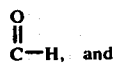

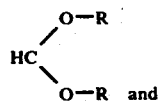

where R' is hydrogen, lower alkyl or substituted lower alkyl and R is alkyl or substituted lower alkyl in a small but effective amount but below the taste threshold to balance coffee flavor.

12. Roasted coffee products having as an active added flavor modifying ingredient a compound selected from the formula:

Where X is selected from the group consisting of CH$_2$OH,

where R' is hydrogen, lower alkyl or substituted lower alkyl and R is alkyl or substituted lower alkyl in a small but effective amount but below the taste threshold to balance coffee flavor.

13. The process of claim 2 in which the compound is 2-(7-methyloct-2-yne) dioxolane.

* * * * *